United States Patent [19]

Walsdorf et al.

[11] Patent Number: 4,895,980

[45] Date of Patent: Jan. 23, 1990

[54] METHOD OF MANUFACTURING MAGNESIUM POTASSIUM CITRATE

[75] Inventors: Neill B. Walsdorf; George Alexandrides, both of San Antonio, Tex.

[73] Assignee: Mission Pharmacal Company, Inc., San Antonio, Tex.

[21] Appl. No.: 303,537

[22] Filed: Jan. 27, 1989

Related U.S. Application Data

[62] Division of Ser. No. 140,818, Jan. 5, 1988.

[51] Int. Cl.⁴ .............................................. C07C 51/43
[52] U.S. Cl. ................................... 562/584; 428/402; 514/574
[58] Field of Search ....................... 562/584; 428/402; 514/574

[56] References Cited

U.S. PATENT DOCUMENTS 3,086,928  4/1963  Schulz ................................. 562/584
4,738,856  4/1988  Clark .................................. 514/574

FOREIGN PATENT DOCUMENTS 968843  4/1958  Fed. Rep. of Germany ...... 562/584
55-108814  8/1980  Japan .................................. 514/574

OTHER PUBLICATIONS

Putzar et al, *Chemical Abstracts*, vol. 90, No. 56264g (1979).

*Primary Examiner*—Bruce Gray
*Attorney, Agent, or Firm*—Ross, Howison, Clapp & Korn

[57] ABSTRACT

A dual mineral salt consisting essentially of magnesium, potassium and citrate. A method for manufacturing the subject salt in a form having a bulk density ranging from about 1.0 g/cc to about 1.3 g/cc is also disclosed, and the use of the subject salt as a dietary supplement are also disclosed.

9 Claims, No Drawings

METHOD OF MANUFACTURING MAGNESIUM POTASSIUM CITRATE

RELATED APPLICATIONS

This is a division of application Ser. No. 07/140,818 filed Jan. 5, 1988 and entitled "Magnesium Potassium Citrate".

TECHNICAL FIELD

This invention relates to dual mineral salts, and more particularly, to a new composition of matter comprising magnesium, potassium and citrate in a single compound. One aspect of the invention relates to the novel salt of the invention, and its method of synthesis. Another aspect of the invention relates to a dietary supplement comprising magnesium, potassium and citrate in a single salt. Another aspect of the invention relates to a magnesium potassium citrate salt having a density preferably greater than about 1.1 g/cc, and to the method of manufacturing tablets from such salt. Still another aspect of the invention relates to a novel method for more effectively supplementing dietary magnesium and potassium by administering magnesium, potassium and citrate in a single salt.

BACKGROUND OF INVENTION

The use of magnesium salts for dietary supplementation is well known. Unfortunately, the beneficial effects derived from dietary magnesium supplementation have too often been achieved at the expense of other undesirable side effects such as acute diarrhea. Another disadvantage of the commercially available dietary magnesium supplements has been the relatively large tablet size required to obtain the desired magnesium dosage.

The use of potassium supplements such as potassium chloride for the treatment of patients with hypokalemia is also well known. Here again, however, problems have been encountered with associated side effects such as arrhythmia and diarrhea.

Recently, it has been learned that some of these undesirable side effects can be better controlled by administering potassium in combination with magnesium citrate. Nevertheless, due to the relatively low densities of the commercially available magnesium citrate preparations, the large tablet sizes required to obtain a desirable dosage remain a problem.

In view of the known medical requirements for potassium and magnesium supplementation under certain circumstances, and in view of recently published data demonstrating the improved uptake and bioavailability of these minerals when administered in combination with citrate, a dietary supplement is therefore needed that comprises magnesium, potassium and citrate in a single salt. A dietary supplement is also needed that comprises a salt containing both potassium and magnesium in a form sufficiently dense that, when tableted, will not require an undesirably large tablet to attain a desired dosage.

SUMMARY OF THE INVENTION

According to the present invention, a novel compound is disclosed that is believed to overcome many of the disadvantages experienced with the prior art compositions.

The present invention is believed to be useful for the manufacture of dietary supplements providing magnesium and potassium, together with citrate, in a single entity. Such supplements might be particularly effective, for example, when administered to patients suffering from electrolyte imbalance while undergoing treatment with diuretics.

According to one embodiment of the invention, a method for synthesizing the magnesium potassium citrate salt of the invention is provided. According to the method of the invention, the subject salt can be produced in an ultradense form having a density ranging from about 1.0 g/cc to about 1.3 g/cc, and preferably greater than about 1.1 g/cc, thereby reducing the tablet size required to attain a desired dosage.

According to another embodiment of the invention, a method is provided for more effectively supplementing dietary magnesium and potassium by administering magnesium, potassium and citrate in a single salt.

The present invention is believed to provide dietary potassium, magnesium and citrate in a form that is more efficiently absorbed than prior art compositions, and with fewer or less severe side effects.

Dietary supplements made with the magnesium, potassium citrate composition of the invention have a satisfactory magnesium/potassium molar ratio, and can be readily compacted into an easily ingestible tablet form. When the subject composition is produced as a pharmaceutical grade, directly compressible material in accordance with a preferred embodiment of the method of the invention, only one or two excipients are required, with no preprocessing.

The invention and the method of practicing it will be better understood upon reading the following description of the preferred embodiments, and by reference to the accompanying examples.

DESCRIPTION OF THE PREFERRED EMBODIMENT

A new compound, a dual mineral salt, has now been synthesized by reacting stoichiometric quantities of citric acid, a magnesium compound and a potassium compound, preferably as follows:

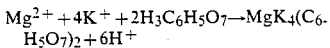

Although the structure of the resultant product is not known with certainty, a likely structural formula for the product is:

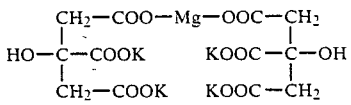

Depending upon reaction conditions and the relative concentrations of the reactants, the monopotassium form of the composition of the invention can also be produced in a competing reaction as follows:

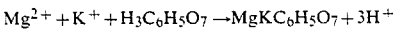

The reaction is preferably initiated by the slow addition of the magnesium compound to a mixture of water and citric acid, followed by the slow introduction of the potassium compound to the reaction mixture.

According to a preferred embodiment of the invention, the magnesium compound is selected from the group consisting of magnesium carbonate, magnesium oxide and magnesium hydroxide. Magnesium oxide is the preferred magnesium compound from a cost standpoint, although the use of magnesium carbonate will provide better control over the temperature of the reaction mixture. The potassium compound is preferably selected from the group consisting of potassium carbonate and potassium bicarbonate, with potassium carbonate being generally preferred because of its lower cost.

The citric acid is mixed with water with uninterrupted agitation, and the magnesium compound and potassium compound are thereafter sequentially mixed with the citric acid to produce a dense, hydrated mixture. This dense hydrated mixture may be characterized as being a thick "slush" comprising magnesium ions, potassium ions and citrate ions in a proportion of about 1:4:2.

During addition of the magnesium compound, the temperature of the mixture is desirably controlled below about 100° C. by controlling the rate of addition. If the temperature of the reaction mixture is permitted to rise above about 120° C., product degradation may occur. A preferred temperature for the reaction mixture during and following addition of the magnesium compound is about 80° C.

The hydrated mixture preferably has a water content between about 10 weight percent and about 20 weight percent. If the water content falls below about 10 weight percent, it is likely that the reaction will be incomplete. Above about 20 weight percent, the mixture retains a paste-like consistency for a longer period of time, which is economically disadvantageous.

This hydrated mixture is thereafter preferably blended in a ribbon mixer to a granular mass consisting of granules and lumps. The mass is then milled and dried to produce a magnesium potassium citrate composition having a maximum particle size of about ⅛ inch (0.3 cm) in diameter and a moisture content ranging between about 0 weight percent and about 5 weight percent. The magnesium potassium citrate composition thus produced has a bulk density (weight per gross volume) preferably ranging from about 1.0 g/cc to about 1.3 g/cc, and most preferably, greater than about 1.1 g/cc. Milling and sizing this bulk material produces a granular pharmaceutical material suitable for tableting.

This bulk magnesium potassium citrate composition is a preferred precursor for the production of magnesium potassium citrate tablets as it represents a densified source of potassium, magnesium and citrate, and is directly compressible. A tableting composition is formed by subjoining and blending it with a lubricant, such as magnesium stearate.

A retarded release tableting composition is formed by subjoining and blending magnesium potassium citrate, a lubricant such as magnesium stearate and a wax material such as carnauba wax. Each of these tableting compositions is then fed through a multiple-station tablet press to form magnesium potassium citrate tablets.

The preferred magnesium potassium citrate tablets thus formed preferably comprise about 27 weight percent potassium, 4 weight percent magnesium, 68 weight percent citrate, and have a magnesium/potassium/citrate molar composition of 1:4:2. Non-wax matrix tablets characteristically have a density of about 1.7 g/cc and wax matrix tablets have a density of about 1.5 g/cc. For aesthetic or other purposes, these tablets may be coated by conventional means with mixtures comprising substances such as sugar, polyvinylpyrrolidone calcium carbonate and titanium oxide, or the like.

The magnesium potassium citrate composition of the invention is a potent delivery system yielding 7.0 meq of potassium (274 mg), 3.5 meq of magnesium (42 mg) and 10.5 meq of citrate (662 mg) in each 10.5 meq tablet of magnesium potassium citrate (978 mg).

The present invention will be better understood by reference to the following examples:

EXAMPLE 1

Citric acid powder (120 g) and water (30 g) were thoroughly mixed in a large beaker. Pure magnesium oxide (12.6 g) was added with rapid stirring. Potassium carbonate powder (86.4 g) was introduced in four approximately equal portions, each portion added after the $CO_2$ evolution had slowed or ceased. Water (10 g) was added to complete the reaction. After drying, the material was sized and found to have a bulk density greater than 1.1 g/cc. Tablet density was determined by an Archimedeah method. This dense granular magnesium potassium citrate was subjected to compression tableting and tablets containing 3.5 meq (42 mg) of magnesium, 7.0 meq (274 mg) of potassium and 10.5 meq (662 mg) of citrate, with a size of 0.28 (7.11 mm) inch by 0.62 (1.6 cm) inch were produced, even without the addition of binders.

EXAMPLE 2

The ultradense magnesium potassium citrate tablets of the invention were also produced on a large scale. Citric acid powder (48.03 kg, 250 moles) and water (12 kg) were placed in a Colton 7 cu. ft. ribbon mixer and blended for 2 minutes. The magnesium oxide (5.04 kg, 125 moles) was added in approximately three equal portions, 3 minutes apart with continuous mixing. Potassium carbonate (69.1 kg, 500 moles) was added in approximately three equal portions 5 minutes apart with continuous mixing. Water (4 kg) was added in order to complete the reaction. Mixing continued for 2–5 minutes. The resultant granular and lumpy material was passed through a Fitzmill, knives forward, with no screen, trayed and dried at 150° F. (66° C.) for three hours. The dried product was sized and its bulk density was determined to be greater than 1.1 g/cc. The sizing was done using a Fitzmill Model No. 6 with a 3162AA screen.

The dried magnesium potassium citrate composition was subjoined with 1.0 weight percent magnesium stearate. The tableting composition was then tableted in a multiple station tablet press to form magnesium potassium citrate tablets comprising at least about 42 mg of magnesium, 274 mg of potassium and 662 mg of citrate. Multiple station tablet presses such as a Cotton #216–16 station press; a Vector #247–41 station press; or a Manesty rotopress-37 station press, for example, may be used. The tablets thus obtained may be final products or may be further processed.

Further processing to physically and aesthetically improve these tablets may be accomplished by tablet coating procedures well known to those skilled in relevant pharmaceutical arts. For example, a coating comprising polyvinylpyrrolidone (PVP), sugar, water, calcium carbonate and titanium dioxide was placed on these tablets. This coating procedure was by conventional pharmaceutical pan-coating technology.

EXAMPLE 3

The procedure from Example 2 was followed with the magnesium oxide being replaced by magnesium carbonate. A magnesium potassium citrate having a bulk density of greater than 1.1 g/cc was produced.

EXAMPLE 4

The procedure from Example 2 was followed with the magnesium oxide being replace by magnesium hydroxide. A magnesium potassium citrate having a bulk density of greater than 1.1 g/cc was produced.

EXAMPLE 5

The procedures of Examples 2, 3 and 4 are followed using potassium bicarbonate instead of potassium carbonate. Again magnesium potassium citrate having a bulk density of greater than 1.1 g/cc is produced.

EXAMPLE 6

Magnesium potassium citrate produced by the methods in Examples 2-5 can be used in the preparation of slow release or retarded release tablets by subjoining it with a mix material such as carnauba wax. The dried, sized magnesium potassium citrate made in accordance with the invention was subjoined with 1.0 weight percent magnesium stearate and 13.2 weight percent carnauba wax. After blending the ingredients for 5 minutes, tableting in the Manesty rotopress yielded tablets having a density of 1.6 g/cc or one tablet per 0.7 cc. Each such tablet contained 978 mg of magnesium potassium citrate and the USP (Method II) dissolution pattern indicated the following:

| Hours Elapsed | Percentage Dissolved |
| --- | --- |
| 0.5 | 35.7 |
| 1.0 | 48.4 |
| 2.0 | 68.5 |
| 3.0 | 81.6 |
| 4.0 | 91.5 |
| 5.0 | 94.8 |
| 6.0 | 100.0 |

This dissolution profile should prevent known side effects encountered with other potassium preparations, despite the fact that the wax level is minimal.

By administering tableted pharmaceutical compositions as disclosed herein, or in such other dosages as may be deemed effective by persons trained in medicine and licensed to prescribe such supplements, it is believed that one can easily supplement dietary magnesium and potassium to a subject in need of such supplementation.

Thus, it is seen that the composition of the present invention provides advantages and benefits not previously available in the production and use of dietary supplements comprising magnesium and potassium. Furthermore, it will be apparent to those skilled in the pharmaceutical arts upon reading this disclosure that other trace elements and minerals can also be compounded with the composition of the invention to produce other useful preparations. For this reason, it is intended that the invention disclosed herein be limited only by the scope of the appended claims.

What is claimed is:

1. A method for producing a magnesium potassium citrate composition comprising the steps of:
   Mixing citric acid and water with uninterrupted agitation;
   While still agitating, gradually adding a magnesium compound and a potassium compound thereto in such proportions that the mixture thus formed comprises magnesium ions, potassium ions and citrate ions in a ratio of about 1:4:2, and the moisture content of the mixture ranges between about 10 weight percent and about 20 weight percent;
   Blending the resultant composition to a granular mass; and thereafter
   Milling and drying the granular mass to form a magnesium potassium citrate composition having the desired particle size and moisture content.

2. The method of claim 1 wherein said magnesium compound is selected from the group consisting of magnesium carbonate, magnesium oxide and magnesium hydroxide.

3. The method of claim 1 wherein said potassium compound is selected from the group consisting of potassium carbonate and potassium bicarbonate.

4. The method of claim 1 wherein the granular mass is milled to a particle size of less that about 0.3 cm. in diameter.

5. The method of claim 1 wherein the granular mass is dried to a moisture content of less than about 5 weight percent.

6. The method of claim 2 wherein the bulk density of said milled and dried granular mass ranges between about 1.0 g/cc and about 1.3 g/cc.

7. The method of claim 6 wherein the bulk density of said milled and dried granular mass is greater than about 1.1 g/cc.

8. The method of claim 7 wherein the bulk density of said milled and dried granular mass is about 1.1 g/cc.

9. The method of claim 1, further comprising the step of tableting said milled and dried granular mass.

* * * * *